(12) United States Patent
Konesky

(10) Patent No.: US 9,387,269 B2
(45) Date of Patent: Jul. 12, 2016

(54) COLD PLASMA JET HAND SANITIZER

(71) Applicant: Bovie Medical Corporation, Clearwater, FL (US)

(72) Inventor: Gregory A. Konesky, Hampton Bays, NY (US)

(73) Assignee: BOVIE MEDICAL CORPORATION, Clearwater, FL (US)

( * ) Notice: Subject to any disclaimer, the term of this patent is extended or adjusted under 35 U.S.C. 154(b) by 295 days.

(21) Appl. No.: 13/802,063

(22) Filed: Mar. 13, 2013

(65) Prior Publication Data

US 2013/0202496 A1    Aug. 8, 2013

Related U.S. Application Data

(63) Continuation-in-part of application No. 13/015,834, filed on Jan. 28, 2011, now Pat. No. 8,795,265.

(60) Provisional application No. 61/645,646, filed on May 11, 2012.

(51) Int. Cl.
| | |
|---|---|
| *A61L 2/14* | (2006.01) |
| *B01J 19/08* | (2006.01) |
| *H05H 1/46* | (2006.01) |
| *A61B 18/00* | (2006.01) |
| *A61L 2/00* | (2006.01) |
| *H05H 1/48* | (2006.01) |

(52) U.S. Cl.
CPC ............. *A61L 2/14* (2013.01); *B01J 19/088* (2013.01); *H05H 1/46* (2013.01); *A61B 2018/00583* (2013.01); *A61L 2/0011* (2013.01); *B01J 2219/0809* (2013.01); *B01J 2219/0828* (2013.01); *B01J 2219/0896* (2013.01); *H05H 2001/466* (2013.01); *H05H 2001/4682* (2013.01); *H05H 2001/483* (2013.01); *H05H 2240/10* (2013.01); *H05H 2240/20* (2013.01); *H05H 2245/1225* (2013.01)

(58) Field of Classification Search
CPC ............................... A61L 2/0094; A61L 2/14
USPC ........................................................ 422/292
See application file for complete search history.

(56) References Cited

U.S. PATENT DOCUMENTS

| | | |
|---|---|---|
| 1,889,609 A | 11/1932 | Mutscheller |
| 2,835,254 A | 5/1958 | Coles |
| 3,299,384 A | 1/1967 | Lee |
| 3,577,030 A | 5/1971 | Cusick et al. |
| 3,601,126 A | 8/1971 | Estes |
| 3,949,266 A | 4/1976 | Vogts et al. |

(Continued)

FOREIGN PATENT DOCUMENTS

WO    2006100030    9/2006

*Primary Examiner* — Sean E Conley
*Assistant Examiner* — Donald Spamer
(74) *Attorney, Agent, or Firm* — Gerald E. Hespos; Michael J. Porco; Matthew T. Hespos

(57) ABSTRACT

A cold plasma jet hand sanitizer and method of use are provided. A pair of opposing two-dimensional arrays of atmospheric pressure cold plasma jets is used to create a sterilizing volume. Any object placed into that volume will have its surface sterilized. The opposing arrays of plasma jets are operated electrically 180 degrees out of phase so that the opposing arrays of plasma jets essentially fire into each other in the absence of an intervening object, or directly impinge on the surface of an intervening object.

18 Claims, 6 Drawing Sheets

A cross-section view of a pair of 2-dimensional plasma jet arrays set in opposition and driven by voltage waveforms 180 degrees out-of-phase.

(56) References Cited

U.S. PATENT DOCUMENTS

| | | | |
|---|---|---|---|
| 3,970,088 A | 7/1976 | Morrison | |
| 3,987,795 A | 10/1976 | Morrison | |
| 4,040,426 A | 8/1977 | Morrison, Jr. | |
| 4,041,952 A | 8/1977 | Morrison, Jr. et al. | |
| 4,043,342 A | 8/1977 | Morrison, Jr. | |
| 4,060,088 A | 11/1977 | Morrison et al. | |
| 4,255,735 A | 3/1981 | Liautaud | |
| 4,429,694 A | 2/1984 | McGreevy | |
| 4,492,231 A | 1/1985 | Auth | |
| 4,547,721 A | 10/1985 | Drapp | |
| 4,559,943 A | 12/1985 | Bowers | |
| 4,781,175 A | 11/1988 | McGreevy et al. | |
| 4,818,916 A | 4/1989 | Morrisroe | |
| 4,887,005 A | 12/1989 | Rough et al. | |
| 4,890,610 A | 1/1990 | Kirwan, Sr. et al. | |
| 4,897,285 A | 1/1990 | Wilhelm | |
| 4,901,719 A | 2/1990 | Trenconsky et al. | |
| 4,901,720 A | 2/1990 | Bertrand | |
| 4,999,597 A | 3/1991 | Gaynor | |
| 5,088,997 A | 2/1992 | Delahuerga et al. | |
| 5,302,881 A | 4/1994 | O'Loughlin | |
| 5,325,019 A | 6/1994 | Miller et al. | |
| 5,669,904 A | 9/1997 | Platt, Jr. et al. | |
| 5,710,486 A | 1/1998 | Ye et al. | |
| 5,717,293 A | 2/1998 | Sellers | |
| 5,720,745 A | 2/1998 | Farin et al. | |
| 5,776,092 A | 7/1998 | Farin et al. | |
| 5,801,489 A | 9/1998 | Chism, Jr. et al. | |
| 5,815,047 A | 9/1998 | Sorensen et al. | |
| 5,909,086 A | 6/1999 | Kim et al. | |
| 5,917,286 A | 6/1999 | Scholl et al. | |
| 6,046,546 A | 4/2000 | Porter et al. | |
| 6,099,523 A | 8/2000 | Kim et al. | |
| 6,135,998 A | 10/2000 | Palanker | |
| 6,154,376 A | 11/2000 | Dan-Harry | |
| 6,161,227 A * | 12/2000 | Bargenquast | 4/622 |
| 6,170,668 B1 | 1/2001 | Babko-Malyi | |
| 6,181,068 B1 | 1/2001 | Hur et al. | |
| 6,213,999 B1 | 4/2001 | Platt et al. | |
| 6,222,321 B1 | 4/2001 | Scholl et al. | |
| 6,262,538 B1 | 7/2001 | Keller | |
| 6,328,760 B1 | 12/2001 | James | |
| 6,387,088 B1 | 5/2002 | Shattuck et al. | |
| 6,492,951 B1 | 12/2002 | Harris et al. | |
| 6,529,389 B2 | 3/2003 | Perlick et al. | |
| 6,627,163 B1 | 9/2003 | Awakowicz et al. | |
| 6,629,974 B2 | 10/2003 | Penny et al. | |
| 6,632,323 B2 | 10/2003 | Kim et al. | |
| 6,764,658 B2 | 7/2004 | Denes et al. | |
| 6,807,069 B2 | 10/2004 | Nieminen et al. | |
| 6,852,112 B2 | 2/2005 | Platt | |
| 6,890,332 B2 | 5/2005 | Truckai et al. | |
| 7,070,144 B1 | 7/2006 | DiCocco et al. | |
| 7,275,013 B1 | 9/2007 | Matlis et al. | |
| 7,316,682 B2 | 1/2008 | Konesky | |
| 7,615,933 B2 | 11/2009 | Hooke et al. | |
| 8,377,388 B2 | 2/2013 | Konesky | |
| 8,388,615 B2 | 3/2013 | Bystryak et al. | |
| 2001/0034519 A1 | 10/2001 | Goble et al. | |
| 2002/0161362 A1 | 10/2002 | Penny et al. | |
| 2002/0187066 A1 | 12/2002 | Yu et al. | |
| 2003/0155332 A1 * | 8/2003 | Datta | A61L 2/14 219/121.52 |
| 2005/0118350 A1 | 6/2005 | Koulik et al. | |
| 2005/0234442 A1 | 10/2005 | Spears | |
| 2005/0241768 A1 * | 11/2005 | Kawamura et al. | 156/345.44 |
| 2006/0005545 A1 | 1/2006 | Samimy et al. | |
| 2007/0089795 A1 | 4/2007 | Jacob | |
| 2008/0000497 A1 * | 1/2008 | Verhaverbeke | 134/1.1 |
| 2009/0119942 A1 | 5/2009 | Aisenberg et al. | |
| 2009/0188626 A1 * | 7/2009 | Lu et al. | 156/345.35 |
| 2009/0304553 A1 | 12/2009 | Gordon | |
| 2010/0296977 A1 | 11/2010 | Hancock | |
| 2011/0171188 A1 | 7/2011 | Morfill et al. | |
| 2011/0184408 A1 | 7/2011 | Konesky et al. | |
| 2011/0277342 A1 | 11/2011 | Ishii et al. | |
| 2012/0039747 A1 | 2/2012 | Morfill et al. | |
| 2012/0046597 A1 | 2/2012 | Morfill et al. | |
| 2012/0046602 A1 | 2/2012 | Morfill et al. | |

* cited by examiner

An array of plasma jets using ballast resistors R1 through Rn.

A cross-section view of a pair of 2-dimensional plasma jet arrays set in opposition and driven by voltage waveforms 180 degrees out-of-phase.

Gas recycling

COLD PLASMA JET HAND SANITIZER

PRIORITY

This application claims priority on U.S. Provisional Patent Appl. No. 61/645,646, filed May 11, 2012, the contents of which are hereby incorporated by reference in its entirety.

This application is also a continuation-in-part application of U.S. patent application Ser. No. 13/015,834, filed Jan. 28, 2011, the contents of which are hereby incorporated by reference in its entirety.

BACKGROUND

1. Field

The present disclosure relates generally to sanitizing systems and apparatuses, and more particularly, to a cold plasma jet hand sanitizer.

2. Description of the Related Art

There are many ways to spread infection from person to person. One of the most common is through direct physical contact, especially in the acquisition of infection. It is generally recommended that a person's hands be washed frequently, however, loss of natural skin oils from frequent washings can lead to dry skin.

This problem is particularly acute in hospitals where doctors and nurses can see many potentially infected patients over the course of a day. Visiting public areas are a cause for concern. Hand-sanitizing liquids may have limited effectiveness, and their frequent use helps breed a population of resistant microorganisms.

Therefore, a need exists for a localized point-of-use system, that is effective in destroying a wide range of microorganisms, and sufficiently gentle that it can be used several times a day, day after day, without negative impact on skin condition.

SUMMARY

The present disclosure relates to a cold plasma jet hand sanitizer and method of use. A pair of opposing two-dimensional arrays of atmospheric pressure cold plasma jets is used to create a sterilizing volume. Any object, e.g., a human hand, placed into the volume, i.e., between the opposing two-dimensional arrays of atmospheric pressure cold plasma jets, will have its surface sterilized. The opposing arrays of plasma jets are operated electrically 180 degrees out of phase so that the opposing arrays of plasma jets essentially fire into each other in the absence of an intervening object, or directly impinge on the surface of an intervening object. The system can be operated continuously, or in an on-demand mode.

The electrically 180 degrees out of phase plasma jets can be achieved by two separate power supplies operated in synchronization with one 180 degrees out-of-phase with the other, or with a low power master oscillator feeding two power driver output stages, where one of these drivers is preceded by a 180 degree phase shift network. Other devices, systems and methods to generate electrically 180 degrees out of phase plasma jets are contemplated to be within the scope of the present disclosure.

In certain embodiments, a gas recycling sub-system or gas reclamation unit is provided and configured to reclaim or scavenge the inert gas used to generate the plasma jets, re-concentrate the reclaimed gas by rejecting atmospheric gas diluents, and then store this recycled gas in, for example, a small compressed gas cylinder for later use. A small door or flap can be used to automatically close an entrance or opening of a housing of the sanitizer while the used helium is being recycled to prevent additional loss through the entrance or opening.

According to one aspect of the present disclosure, a cold plasma hand sanitizer includes a first gas manifold including a first plurality of output channels formed on at least one surface of the first gas manifold, each of the first plurality of output channels including an individual wire electrode disposed therein, wherein a plasma jet is formed at each output channel when gas is supplied to the output channels and a first common power supply of high voltage at high frequency is applied to the electrodes of the first gas manifold; and a second gas manifold including a second plurality of output channels formed on at least one surface of the second gas manifold, each of the second plurality of output channels including an individual wire electrode disposed therein, wherein arrays of plasma jets are formed at each output channel when gas is supplied to the output channels and a second common power supply of high voltage at high frequency is applied to the electrodes of the second gas manifold, each of the second plurality of output channels being configured to face and aligned with a corresponding output channel of the first plurality of output channels; wherein the first common power supply is 180 degrees out of phase relative to the second common power supply.

BRIEF DESCRIPTION OF THE DRAWINGS

The above and other aspects, features, and advantages of the present disclosure will become more apparent in light of the following detailed description when taken in conjunction with the accompanying drawings in which.

Figure 1:
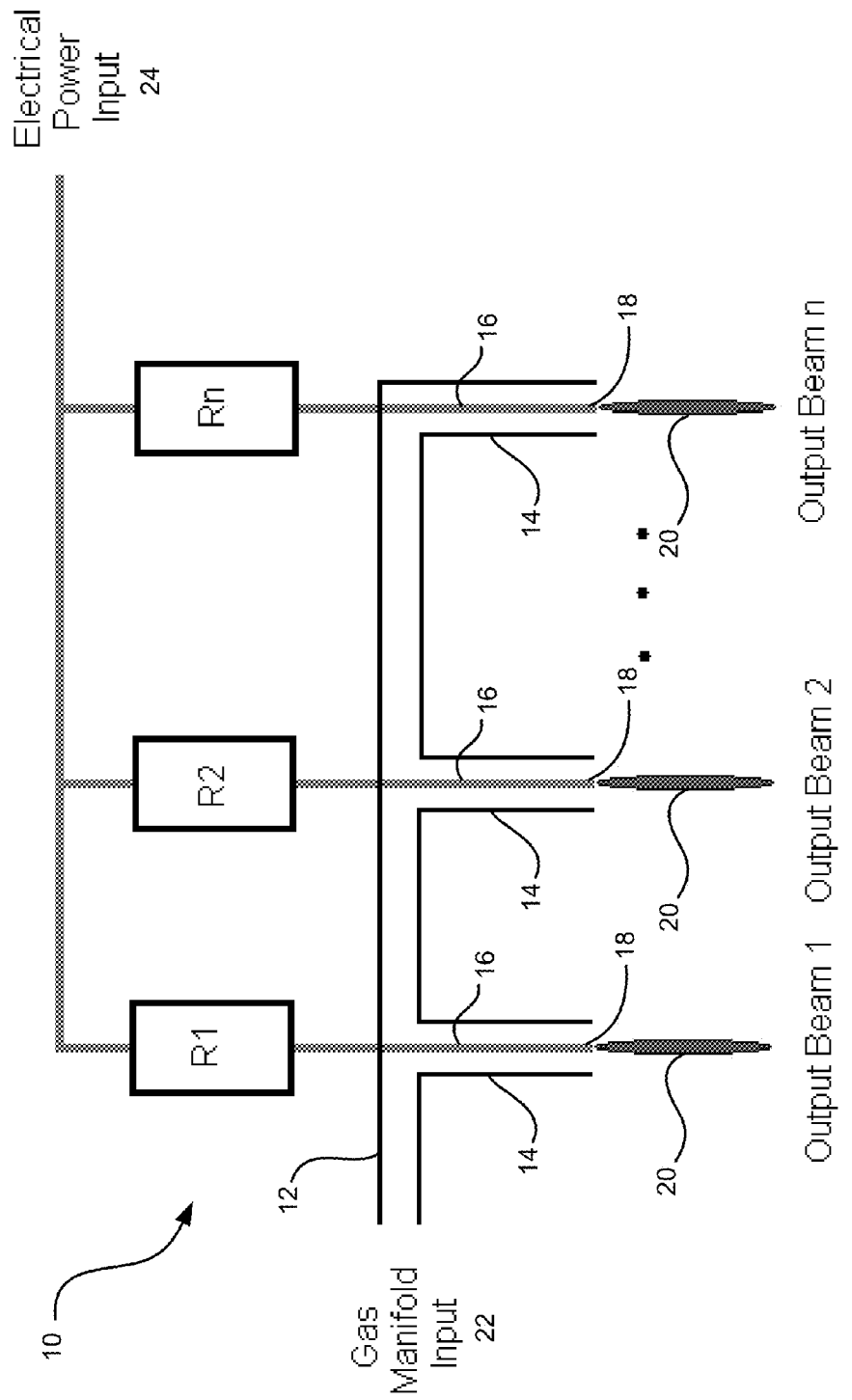
FIG. 1 is an illustration of an array of plasma jets in accordance with an embodiment of the present disclosure.

It should be understood that the drawing(s) is for purposes of illustrating the concepts of the disclosure and is not necessarily the only possible configuration for illustrating the disclosure.

DETAILED DESCRIPTION

Preferred embodiments of the present disclosure will be described hereinbelow with reference to the accompanying drawings. In the following description, well-known functions or constructions are not described in detail to avoid obscuring the present disclosure in unnecessary detail. In the drawings and in the description which follow, the term "proximal", as is traditional, will refer to the end of the device, e.g., instrument, apparatus, applicator, handpiece, forceps, etc., which is closer to the user, while the term "distal" will refer to the end which is further from the user. Herein, the phrase "coupled" is defined to mean directly connected to or indirectly connected with through one or more intermediate components. Such intermediate components may include both hardware and software based components.

Atmospheric pressure, non-thermal, cold plasma discharge jets are formed by passing a stream of inert gas, typically either helium or argon, over a sharp conductive point that is held at high voltage and high frequency. A small fraction of the flowing gas is ionized, producing a luminous discharge jet at atmospheric pressure. Typically, between one gas molecule in $10^3$ and one in $10^6$ is ionized, and most of the energy is carried by the electrons in this plasma discharge. Consequently, the bulk of the gas flowing in the plasma jet is at or near ambient temperature, qualifying it for the terms non-thermal and cold plasma discharge.

Referring to FIG. 1, a system 10 for producing atmospheric pressure, non-thermal, cold plasma discharge jets is illustrated. The system 10 includes a gas manifold 12 including a plurality of output channels 14 formed on at least one surface of the gas manifold 12. Each output channel 14 includes an individual wire electrode 16 with a sharp conductive point 18 concentrically disposed therein. Arrays of plasma jets 20 are formed at each output channel 14 when gas is supplied from a common gas supply via a gas manifold input 22 and common power supply of high voltage at high frequency is applied to the electrodes 16 with the sharp conductive points 18. It is to be appreciated that the common gas supply feeds gas from a single source to the plurality of output channels and the common power supply supplies voltage to each of the electrodes at the same potential and phase.

A plasma beam can be formed by passing the gas over the sharp conductive point, which is held at a relatively high voltage, generally greater than 1 KV, and at a relatively high frequency, generally in the range of approximately 10 KHz to approximately 10 GHz. The sharp conductive point creates a strong electric field gradient which helps pull electrons off the inert gas molecules and ionize the electrons.

However, plasma jet discharges exhibit a dynamic negative resistance. As the current flowing through a plasma discharge increases, the voltage drop across it decreases since more of the flowing gas becomes ionized, providing more conductive paths and reducing the equivalent plasma resistance. This results in one of the plurality of conductive points firing and producing a plasma jet, but also reducing the voltage so that no other conductive points will fire. To prevent this, a ballast resistor R1, R2 ... Rn is placed in series with each conductive point 18, balancing the voltage distribution among them, and ensuring that all points will fire and produce an array of plasma jets.

Figure 2A:
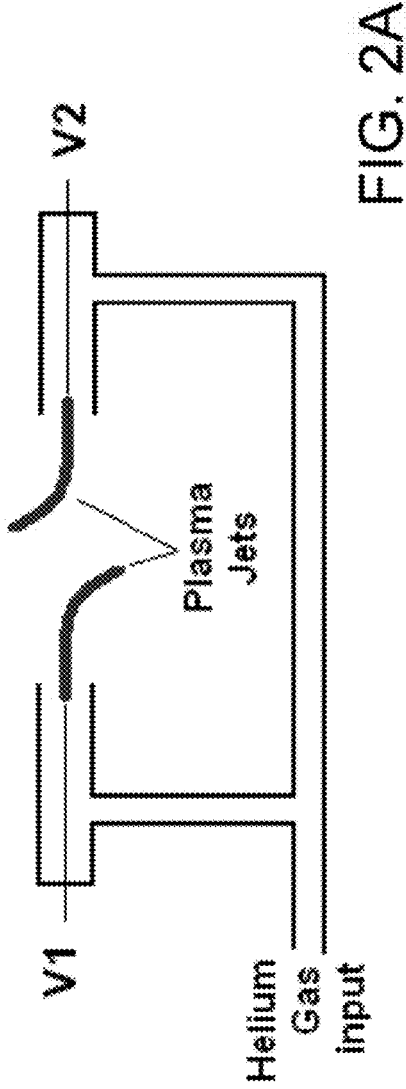
FIGS. 2A-B are illustrations of the effect of in-phase (FIG. 2A) and out-of-phase (FIG. 2B) voltage waveforms on a pair of opposing plasma jets in accordance with an embodiment of the present disclosure.
Figure 2A:
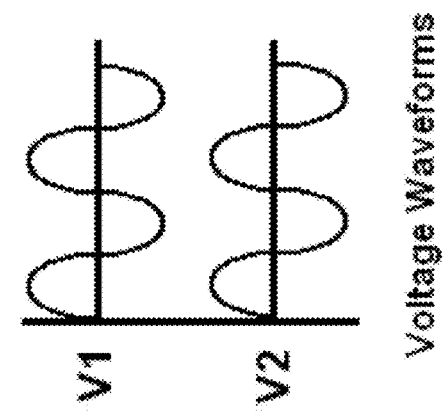

If two plasma jets are pointed toward each other and operated from the same power supply, the plasma jets will "avoid" each other, as shown in FIG. 2A. Since the electrodes are connected to the same power supply, through ballast resistors, the plasma jets will be firing in-phase, e.g., in-phase voltage waveforms of FIG. 2A. In one half cycle of the high voltage high frequency power supply, both plasma jets will be positively charged, for example, and during the next half cycle, both will be negatively charged. Since like-charges repel, these in-phase plasma jets will avoid each other.

Figure 2B:
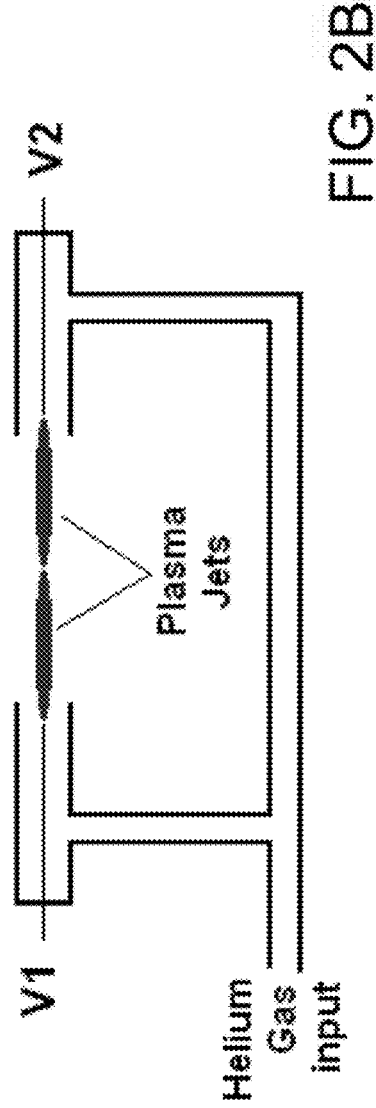
Figure 2B:
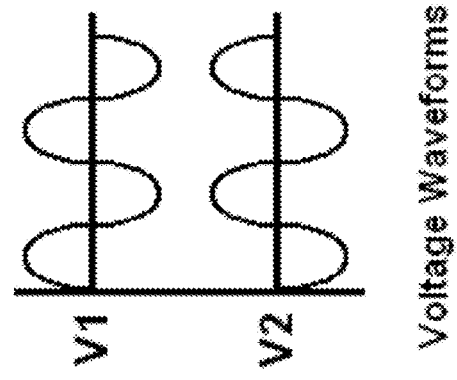

If the electrical power to one of the opposing pair of plasma jets is phase shifted by 180 degrees, they will directly fire into each other since opposite-charges attract, as shown in FIG. 2B. It is to be appreciated that the term "phase shifted by 180 degrees" refers to the driving voltage waveforms at each electrode generating the respective plasma beams or jets, although the current waveforms are also 180 degrees out of phase relative to each other. The out-of-phase voltage waveforms are illustrated in FIG. 2B.

As described above, arbitrarily large arrays of plasma jets can be formed using ballast resistors. They can be assembled into a linear line array, or a 2-dimensional planar array. A pair of planar arrays can be set in opposition and operated electrically out-of-phase so that a dense network of plasma jets firing into and interconnecting with opposing jets will be formed, as shown in FIG. 3.

Cold plasma jets have two independently controllable variables, permitting a wide range of effects. One is the electrical power to create the plasma jet, and the other is the gas flow rate. When the electrical power is high and the gas flow rate is low, an intense burning beam results. This has been used in medical applications to ablate tumors, for example. On the other hand, when the electrical power is low, and the gas flow rate is high, a gentle sterilizing beam results which is effective on a wide range of microorganisms, including human pathogens. The sterilization effect is produced by a concert of plasma beam effects including ion bombardment, electron bombardment, free radicals, localized UV exposure, thermal effects, localized ozone production, electroporation and disruption of microorganism outer membranes by electrostatic fields.

Figure 3:
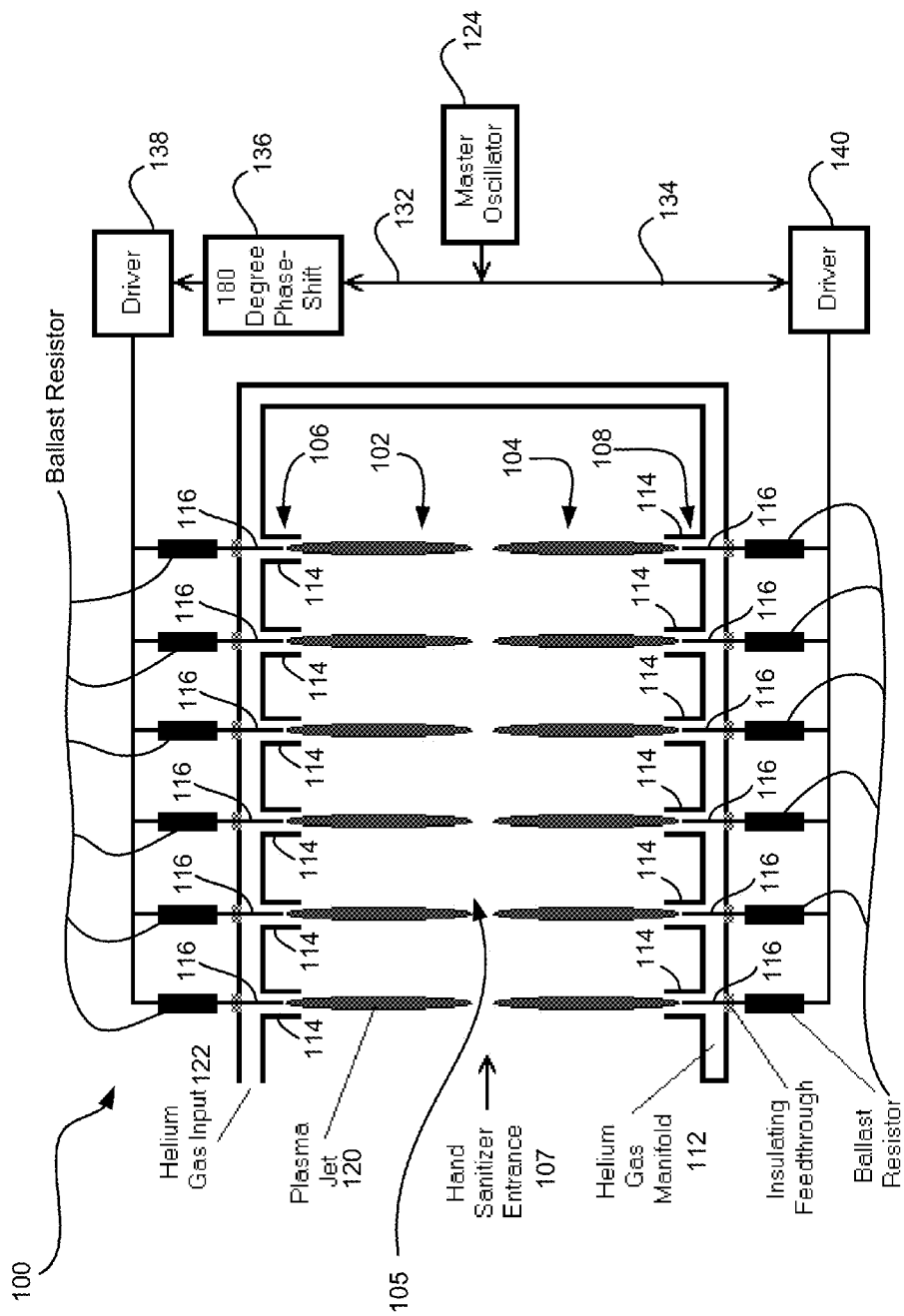
FIG. 3 is a cross sectional view of a cold plasma jet hand sanitizer in accordance with an embodiment of the present disclosure.

Referring to FIG. 3, a cold plasma jet hand sanitizer 100 is illustrated. The sanitizer 100 includes a pair of opposing two-dimensional arrays 102, 104 of atmospheric pressure cold plasma jets to create a sterilizing volume 105. Any object placed into that volume 105 will have its surface sterilized. In the embodiment shown, the sanitizer 100 includes a gas manifold 112 configured with a pair of opposing two-dimensional arrays 106, 108 of output channels 114. It is to be appreciated that the output channels 114 of each array 106, 108 are aligned with each other to align the plasma jets when fired. It is further to be appreciated that although the gas manifold is shown as a single unit with a single gas input 122, the arrays may be configured as two separate manifolds each with a gas input.

The opposing arrays 106, 108 of plasma jets are operated electrically 180 degrees out of phase so that the opposing arrays essentially fire into each other in the absence of an intervening object, or directly impinge on the surface of an intervening object. As shown in FIG. 3, a master oscillator 124 is provided to provide high frequency, high voltage to each electrode 116 disposed in each output channel 114. The output from the master oscillator 124 is split into two paths 132, 134. The output of the first path 132 is transmitted to a phase shifter 136 which shifts the phase of the voltage signal a predetermined amount, e.g., about 180 degrees. The shifted voltage signal is then provided to driver 138 which transmits the shifted voltage signal to the electrodes 116 of the first array 106. The output of the second path 134 is transmitted to driver 140 which transmits the non-shifted voltage signal to the electrodes 116 of the second array 108. Other systems, circuits and methods for generating at least two voltage waveforms 180 degrees out of phase relative to each other are contemplated by the present disclosure.

It is to be appreciated that the master oscillator 124, phase shifter 136 and drivers 138, 140 may be configured as a power or electrosurgical generator, as shown and described in copending U.S. patent application Ser. No. 13/015,834, the contents of which are hereby incorporated by reference in its entirety.

While helium is the preferred carrier gas, other inert gases, such as argon, or air may be used individually, or in combination. The addition of a small amount of oxygen to an inert gas significantly enhances its effectiveness.

Gas consumption is an important issue, particularly at a remote site. While argon may be scavenged from the atmosphere, where it contributes approximately 0.9% by volume, helium is much rarer, typically only about 5 ppm. Since the helium gas released into the sterilizing volume will be at a high concentration in that volume, a means may be provided to collect and re-concentrate it, and then store it for later use, e.g., a reclamation unit.

Figure 4:
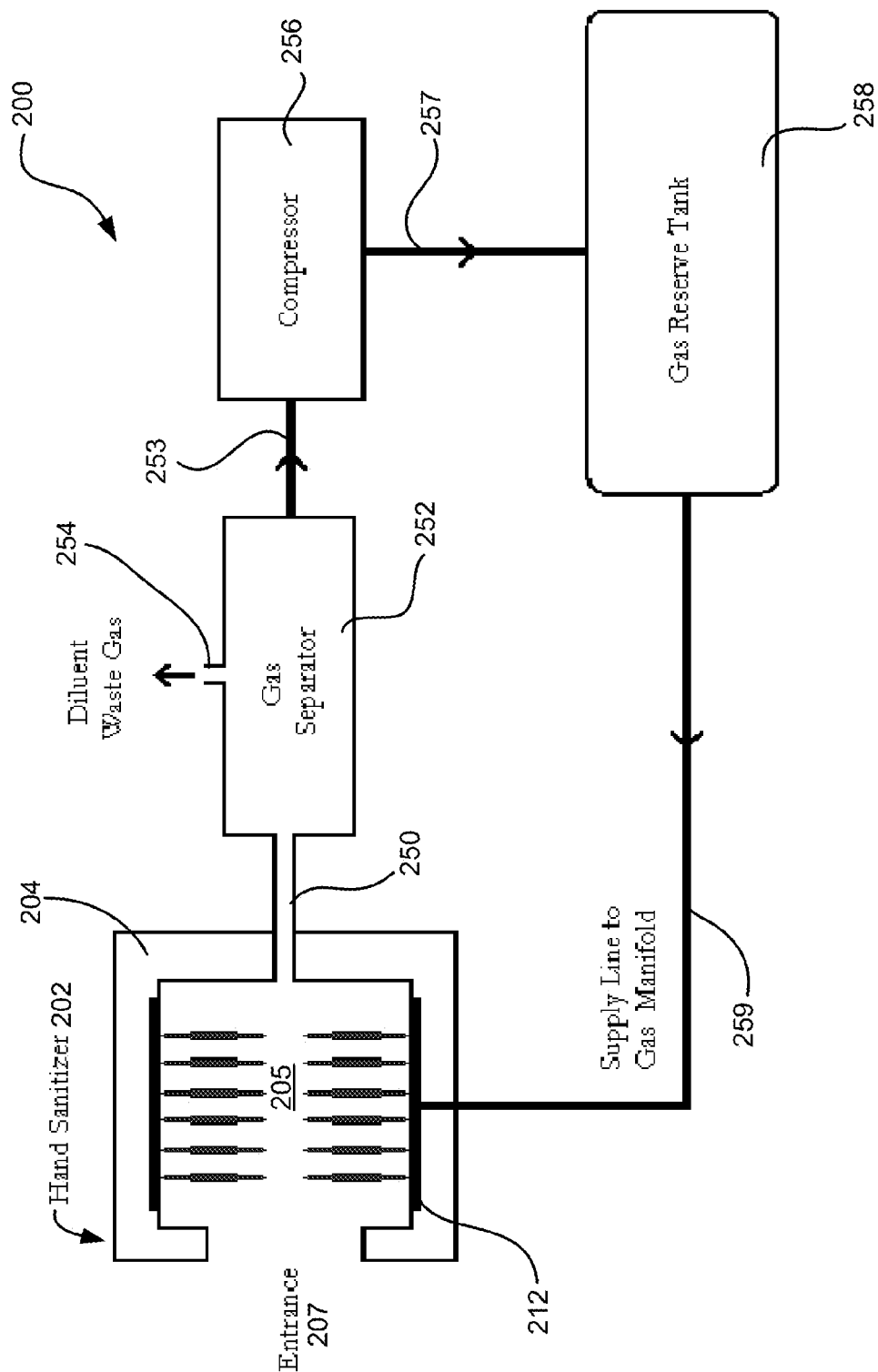
FIG. 4 is an illustration of a cold plasma jet hand sanitizer in accordance with another embodiment of the present disclosure.

Referring to FIG. 4, a system 200 including a cold plasma jet hand sanitizer with gas reclamation is illustrated. The hand sanitizer 202 includes substantially the same components as described above for hand sanitizer 100 shown in FIG. 3. In this embodiment, the hand sanitizer 202 includes a housing 204 for containing gas discharged during the sanitizing process. In one embodiment, the housing 204 may be generally rectangular or cubical in shape including an opening or entrance 207 for allowing an object, e.g., a hand, to pass through. It is to be appreciated that other shapes for the housing are contemplated to be within the scope of the present disclosure.

The housing 204 further includes a channel or conduit 250 configured for withdrawing gas used during a sanitizing process from the volume 205 within the housing 204. The channel 250 is coupled to a gas separator 252. Helium, due to its small molecular diameter, is especially amenable to re-concentration through a diffusion membrane of the gas separator 252 which allows the helium to pass through, but rejects the diluent atmospheric gases, such as nitrogen and oxygen, via output port 254. A compressor 256 receives the reclaimed gas from the gas separator 252 via conduit 253 then stores this recycled inert gas in a gas reserve tank 258, e.g., a small pressure cylinder, via conduit 257 for later use. The recycled inert gas can then be provided to the gas manifold 212 of the hand sanitizer via conduit 259 for subsequent sanitizing procedures.

In certain embodiments, the reclamation unit may be configured as a external unit including the gas separator 252, compressor 256, gas reserve tank 258 and various conduits.

Figure 5A:
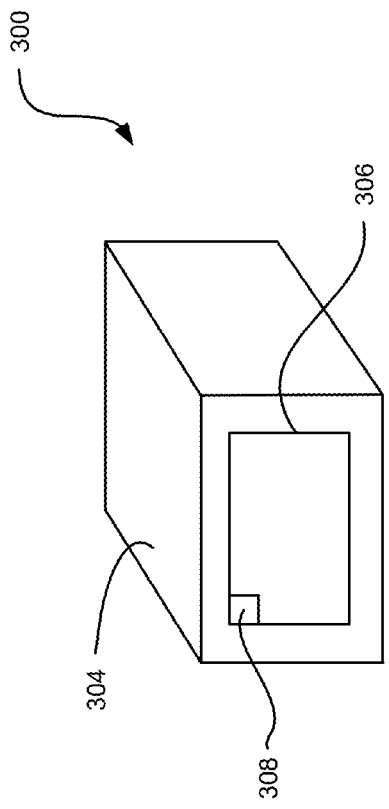
FIGS. 5A-B are illustrations of a cold plasma jet hand sanitizer in accordance with a further embodiment of the present disclosure.
Figure 5B:
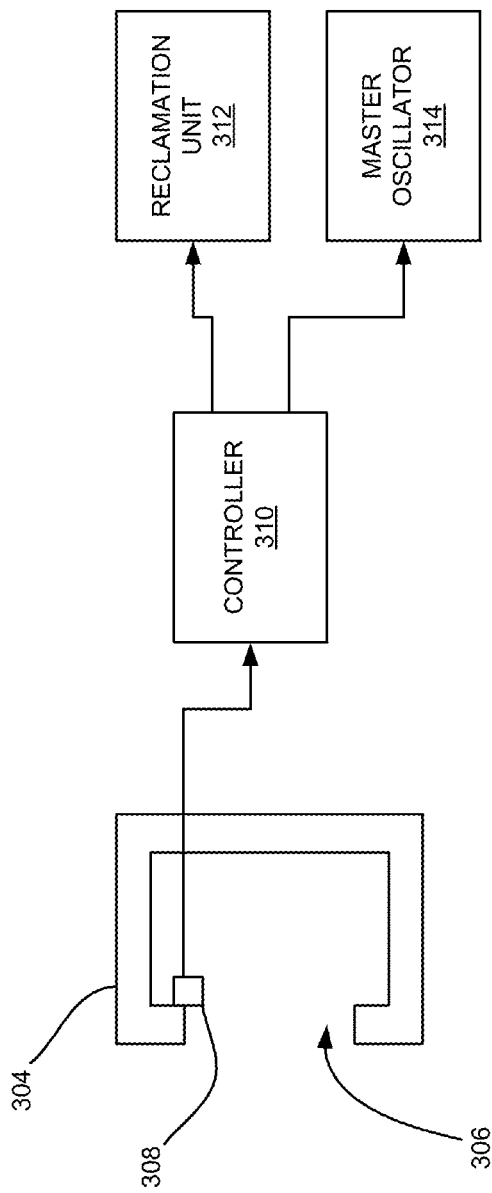

In portable or point-of-use applications, inert gas consumption from reservoir tanks may become an issue. To limit gas use, an on-demand control is employed, such as a photosensor or proximity detector so that the system is activated only as needed. For example, as shown in FIG. 5A, a sanitizing system 300 is configured with a generally rectangular housing 304 with at least one opening 306 to allow an object, for example, a human hand, to be disposed between the two plasma jets arrays to be sanitized. A photosensor or proximity detector 308 is disposed adjacent the opening 306 so that the system is activated only as needed. The detector 308 is configured to detect an object and initiate gas flow and power supplied to the electrodes. It is to be appreciated that the detector 308 may be hardwired to initiate the gas flow and supplying of power. In one embodiment, as shown in FIG. 5B, the detector 308 may generate a signal that is supplied to a controller 310 that initiates the gas flow via the gas reclamation unit 312 and supplying of power via the master oscillator 314.

Figure 6A:
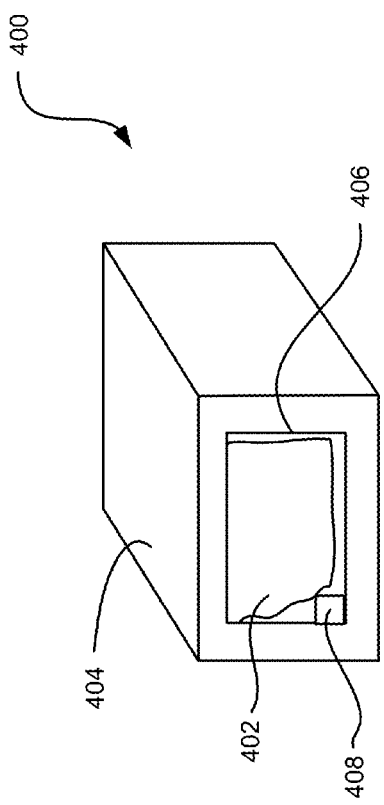
FIGS. 6A-B are illustrations of a cold plasma jet hand sanitizer in accordance with yet another embodiment of the present disclosure.
Figure 6B:
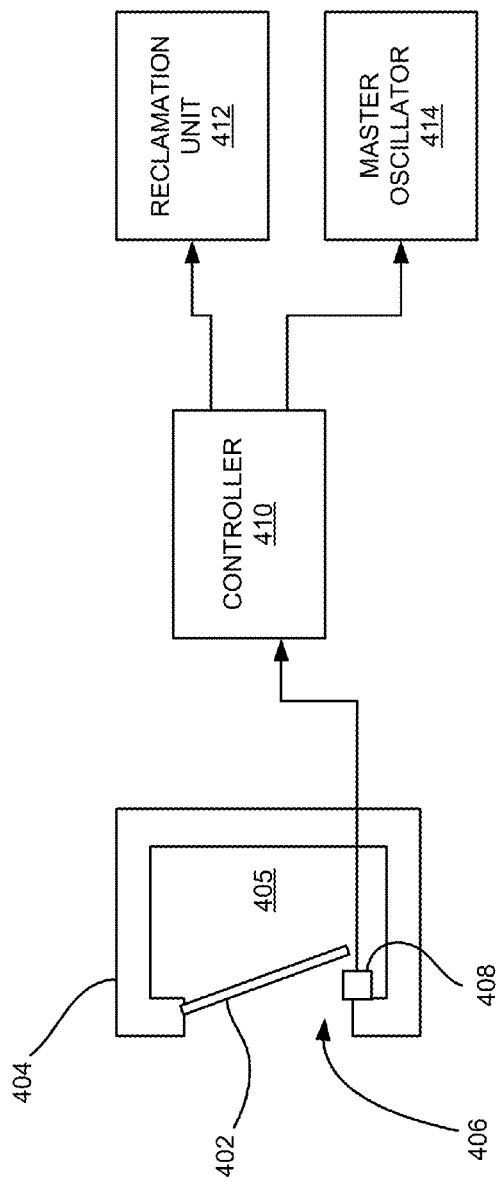

In a further embodiment, as shown in FIGS. 6A-B, a sanitizing system 400 includes a small door or flap member 402 that automatically closes an entrance or opening 406 of the housing 404 after the hand or object is removed, isolating the volume 405 of concentrated helium while it is being recycled, and preventing further escape of helium through the entrance 406. A switch 408 may be coupled to the door or flap member 402 to determine use of the hand sanitizer creating an on-demand mode. For example, upon placing an object in the opening 406, the door or flap member 402 will open causing the switch 408 to close. Upon closure of the switch 408, a controller 410 initiates the gas flow via the gas reclamation unit 412 and supplying of power via the master oscillator 414 causing the plasma jets to fire. Upon removal of the object, the door or flap member 402 will close and the switch 408 will open. Upon the switch 408 opening, the master oscillator 414 will be de-energized, via the controller 410, and the compressor of the reclamation unit 412 will be energized for a predetermined period of time to recycle the gas in the volume 405. After the predetermined period of time has expired, the compressor will be de-energized.

It is to be appreciated that due to the structure of the housing 404, i.e., having five closed walls with one opening 406 and a flap member 402, most of the gas used during a sanitizing procedure remains within the volume 405 for possible reclamation.

Cold plasma discharges have been shown to be effective against the microorganism Deinococcus radiodurans, which was first discovered in the intensively radioactive cooling pools of used nuclear reactor fuel rods. Deinococcus radiodurans can continuously absorb 6,000 rads/hour without mutations or effect on its growth rate, and can survive a single burst of 1,500,000 rads. The human single burst lethal dose, for comparison, is between 2,000 and 5,000 rads.

In addition to its sterilization effects, cold plasma discharges have been used to decontaminate various toxic chemicals and agents, including chemical and biological warfare agents. Cold plasma discharges can also be useful in assisting in the clean up of radiological agents such as a "dirty bomb" by helping to liberate radioactive particles from contaminated surfaces, which are subsequently collected and disposed of.

Since cold plasma discharges can be effective in decontaminating surfaces without damaging those surfaces, especially on delicate materials, these discharges have been tested for use in decontaminating spacecraft for the Planetary Protection Protocol. This protocol addresses forward-contamination, to prevent microorganisms from Earth from contaminating another planet, and back-contamination where the exterior of a sample return container must be thoroughly decontaminated before return to Earth.

In addition to sanitizing hands, such a system can be used to sterilize and decontaminate a variety of objects such as surgical instruments, tools, components, growth media, pharmaceuticals, and so on.

It will be appreciated by those skilled in the art that the block diagrams presented herein represent conceptual views of illustrative circuitry embodying the principles of the disclosure. Similarly, it will be appreciated that any flow charts, flow diagrams, state transition diagrams, pseudo-code, and the like represent various processes which may be substantially represented in computer readable media and so executed by a computer or processor, whether or not such computer or processor is explicitly shown.

The functions of the various elements shown in the figures may be provided through the use of dedicated hardware as well as hardware capable of executing software in association with appropriate software. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor ("DSP") hardware, read only memory ("ROM") for storing software, random access memory ("RAM"), and nonvolatile storage.

Other hardware, conventional and/or custom, may also be included. Similarly, any switches shown in the figures are conceptual only. Their function may be carried out through the operation of program logic, through dedicated logic, through the interaction of program control and dedicated logic, or even manually, the particular technique being selectable by the implementer as more specifically understood from the context.

It is to be appreciated that the various features shown and described are interchangeable, that is a feature shown in one embodiment may be incorporated into another embodiment.

While the disclosure has been shown and described with reference to certain preferred embodiments thereof, it will be understood by those skilled in the art that various changes in form and detail may be made therein without departing from the spirit and scope of the disclosure.

Furthermore, although the foregoing text sets forth a detailed description of numerous embodiments, it should be understood that the legal scope of the invention is defined by the words of the claims set forth at the end of this patent. The detailed description is to be construed as exemplary only and does not describe every possible embodiment, as describing every possible embodiment would be impractical, if not impossible. One could implement numerous alternate embodiments, using either current technology or technology developed after the filing date of this patent, which would still fall within the scope of the claims.

It should also be understood that, unless a term is expressly defined in this patent using the sentence "As used herein, the term '_____' is hereby defined to mean . . . " or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning. Finally, unless a claim element is defined by reciting the word "means" and a function without the recital of any structure, it is not intended that the scope of any claim element be interpreted based on the application of 35 U.S.C. §112, sixth paragraph.

What is claimed is:

1. A cold plasma sanitizing device comprising:
a first gas manifold including a first gas input conduit and a plurality of first gas output conduits, wherein gas introduced into the first gas input conduit exits the first gas manifold through the plurality of first gas output conduits;
a first plurality of wire electrodes, wherein each wire electrode of the first plurality of wire electrodes is disposed within a respective first gas output conduit of the plurality of first gas output conduits;
a first common power supply configured to provide a high voltage output at a high frequency, wherein a plasma jet is formed at an output of each of the plurality of first gas output conduits when gas is introduced into the first gas input conduit and the first common power supply provides the high voltage output at the high frequency to the first plurality of wire electrodes;
a second gas output manifold including a second gas input conduit and a plurality of second gas output conduits, wherein gas introduced into the second gas input conduit exits the second gas manifold through the plurality of second gas output conduits;
a second plurality of wire electrodes, wherein each wire electrode of the second plurality of wire electrodes is disposed within a respective second gas output conduit of the plurality of second gas output conduits; and
a second common power supply configured to provide a high voltage output at a high frequency, wherein a plasma jet is formed at an output of each of the plurality of second gas output conduits when gas is introduced into the second gas input conduits and the second common power supply provides the high voltage output at the high frequency to the second plurality of wire electrodes;
wherein the output of each of the plurality of second gas output conduits faces and is longitudinally aligned with the output of a corresponding first gas output conduit such that the plasma jet formed at the output of each of the plurality of first as output conduits is directed toward the plasma jet formed at the output of the corresponding second gas output conduit;
wherein the first common power supply supplies power 180 degrees out of phase with respect to the second common power supply.

2. The cold plasma sanitizing device as in claim 1, wherein the first and second gas manifolds are configured as a single unit having a common gas input configured to feed the first and second gas input conduits.

3. The cold plasma sanitizing device as in claim 1, further comprising an oscillator configured to supply high frequency voltage, wherein the oscillator is coupled to the first common power supply and coupled via a phase shifter to the second common power supply.

4. The cold plasma sanitizing device as in claim 1, further comprising a housing configured to support the first gas manifold on an opposite side from the second gas manifold such that the output of each of the plurality of second gas output conduits faces and is longitudinally aligned with the output of a corresponding first gas output conduit.

5. The cold plasma sanitizing device as in claim 4, wherein the housing includes at least one opening to allow an object to be disposed in a volume between the first and second gas manifolds, wherein the plasma jets are configured to sanitize at least one surface of the object.

6. The cold plasma sanitizing device as in claim 5, further comprising a gas reclamation unit configured to reclaim the gas discharged via the plurality of first and second gas output conduits.

7. The cold plasma sanitizing device as in claim 6, wherein the gas reclamation unit includes a discharge conduit coupled to the housing configured to withdraw gas from the volume within the housing.

8. The cold plasma sanitizing device as in claim 7, wherein the gas reclamation unit includes a gas separator coupled to the discharge conduit, the gas separator configured to separate the gas from atmospheric gases.

9. The cold plasma sanitizing device as in claim 5, wherein the housing includes a proximity detector adjacent the opening to detect the object, and wherein, upon detection of the object, a controller is configured to initiate gas flow to the first and second gas input conduits and to instruct the first and second common power supplies to provide power.

10. The cold plasma sanitizing device as in claim 6, wherein the housing includes a flap member adjacent the opening and configured to seal the opening to isolate gas within the housing when the object is removed from the housing.

11. The cold plasma sanitizing device as in claim 10, further comprising a switch coupled to the flap member configured to determine if the flap member is open or closed relative to the opening.

12. The cold plasma sanitizing device as in claim 11, wherein, when the flap member is open, a gas flow to the first and second gas input conduits is initiated and the first and second common power supplies provide power.

13. The cold plasma sanitizing device as in claim 12, wherein, when the flap member is closed, the gas flow is ceased and power is ceased.

14. The cold plasma sanitizing device as in claim 13, wherein, when the flap member is closed, the gas reclamation unit is activated for a predetermined period of time.

15. The cold plasma sanitizing device as in claim 1, wherein the first plurality of gas output conduits are arranged in the first gas manifold in a two-dimensional array and the second plurality of gas output conduits are arranged in the second gas manifold in a two-dimensional array facing the gas output conduits of the first plurality of gas output conduits.

16. A cold plasma sanitizing device comprising:
a housing configured to support a first gas manifold at a predetermined distance opposite a second gas manifold, wherein a sanitizing volume is defined between the first and second gas manifolds;
the first gas manifold including a first gas input conduit and a plurality of first gas output conduits, wherein gas introduced into the first gas input conduit exits the first gas manifold through the plurality of first gas output conduits;
a first plurality of wire electrodes, wherein each wire electrode of the first plurality of wire electrodes is disposed within a respective first gas output conduit of the plurality of first gas output conduits;
a first common power supply configured to provide a high voltage output at a high frequency, wherein an atmospheric pressure cold plasma jet is formed at an output of each of the plurality of first gas output conduits when gas is introduced into the first gas input conduit and the first common power supply provides the high voltage output at the high frequency to the first plurality of wire electrodes; and
the second gas manifold including a second gas input conduit and a plurality of second gas output conduits, wherein gas introduced into the second gas input conduit exits the second gas manifold through the plurality of second gas output conduits;
a second plurality of wire electrodes, wherein each wire electrode of the second plurality wire electrodes is disposed within a respective second gas output conduit of the plurality of second gas output conduits;
a second common power supply configured to provide a high voltage output at a high frequency, wherein an atmospheric pressure cold plasma jet is formed at an output of each of the plurality of second gas output conduits when gas is introduced into the second gas input conduits and the second common power supply provides the high voltage output at the high frequency to the second plurality of wire electrodes;
wherein the output of each of the plurality of second gas output conduits faces and is longitudinally aligned with the output of a corresponding first gas output conduit such that the plasma jet formed at the output of each of the plurality of first as output conduits is directed toward the plasma jet formed at the output of the corresponding second gas output conduit;
wherein the first common power supply supplies power 180 degrees out of phase with respect to the second common power supply so each of the atmospheric pressure cold plasma jets formed at each of the second plurality of gas output conduits fires into the atmospheric pressure cold plasma jets formed at the corresponding gas output conduit of the first plurality of gas output conduits.

17. The cold plasma sanitizing device as in claim 16, wherein the high voltage output is greater than 1 KV.

18. The cold plasma sanitizing device as in claim 17, wherein the high frequency is in a range of approximately 10 kHz to approximately 10 GHz.

* * * * *